United States Patent [19]

Omura et al.

[11] Patent Number: 5,488,125
[45] Date of Patent: Jan. 30, 1996

[54] METHOD FOR MANUFACTURING ORGANOSILANES HAVING SILANOL GROUPS

[75] Inventors: Naoki Omura, Akron, Ohio; Minoru Igarashi, Gunma, Japan; Yoshio Inoue, Gunma, Japan; Masaharu Takahashi, Gunma, Japan

[73] Assignee: Shin-Etsu Chemical Co., Ltd., Tokyo, Japan

[21] Appl. No.: 392,116

[22] Filed: Feb. 22, 1995

[30] Foreign Application Priority Data

Feb. 23, 1994 [JP] Japan .................. 6-049820

[51] Int. Cl.$^6$ .................................................. C07F 7/08
[52] U.S. Cl. .................................................. 556/463
[58] Field of Search .................................... 556/463

[56] References Cited

U.S. PATENT DOCUMENTS

| | | | |
|---|---|---|---|
| 2,438,055 | 3/1948 | Hyde et al. .............. | 556/463 |
| 3,304,318 | 2/1967 | Brady . | |
| 3,364,246 | 1/1968 | Rossmy .................... | 556/463 |
| 3,925,825 | 12/1975 | Richards et al. . | |
| 4,207,247 | 6/1980 | Knollmueller .............. | 556/463 |
| 4,395,563 | 7/1983 | Hayes ...................... | 556/463 X |
| 4,517,375 | 5/1985 | Schmidt .................... | 556/463 |
| 5,057,620 | 10/1991 | Inoue et al. . | |

*Primary Examiner*—Paul F. Shaver
*Attorney, Agent, or Firm*—Millen, White, Zelano, & Branigan

[57] ABSTRACT

A manufacturing method of organosilanes having silanol groups which is characterized by mixing organoalkoxy silanes, having at most a 20 ppm content of chlorine, expressed by the general chemical formula (1) below:

$$Si(R^1)_m(R^2)_n(OR^3)_k \qquad (1)$$

wherein each of $R^1$ and $R^2$ is either a substituted or unsubstituted monovalent hydrocarbon group; $R^3$ is an alkyl group of 1 to 4 carbon atoms; subscripts m and n are 0, 1, 2, or 3; k is either 1 or 2; and the sum of subscripts m+n+k=4, with ion-exchanged water having an electroconductivity of at least $10^{10} M\Omega$, then further adding a macro-porous cation-exchange resin with a pore volume measured by the mercury injection method of at least 0.1 ml/g to the said mixture, followed by stirring of the mixture and removal of the cation-exchange resin. According to the present invention, organosilanes having silanol groups which are useful as a dispersing agent in silicone rubbers may be obtained by a simple process from organoalkoxy silanes, such as relatively inexpensive dimethoxy dimethyl silane.

17 Claims, No Drawings

METHOD FOR MANUFACTURING ORGANOSILANES HAVING SILANOL GROUPS

BACKGROUND OF THE INVENTION

This invention relates to methods for manufacturing silanes having silanol groups by using organoalkoxy silanes as a starting material.

Linear organopolysiloxanes having hydroxyl groups at both molecular ends are useful as dispersing agents in the manufacturing of silicone rubber compounds, and various kinds of dispersing agents have been employed. The effectiveness of the dispersing agents is proportional to the content of the hydroxyl groups. Therefore, a polysiloxane having more hydroxyl groups in its content, that is, a low molecular weight linear organosiloxane having silanol groups as its terminal groups can be used in a lesser amount and is thus more effective from the processability viewpoint of the silicone rubber compounds. However, linear organopolysiloxanes currently employed on an industrial level are organotetrasiloxanes or larger. There have been hardly any proposals to obtain more effective lower molecular weight organosilanes or siloxanes having silanol groups, such as monomer diols, dimer diols, and trimer diols, on an industrial level having the indicted advantages.

Conventionally, much research has been carried out on synthesis methods for short-chained hydroxy silanes and siloxanes. In the laboratory, a known method is to hydrolyze alkoxy silanes while maintaining the solution neutral by employing, for example, a buffer solution. However, this method is difficult to perform on an industrial level. A further method includes refluxing dimethoxy silane which is mixed with neutral distilled water in excess, however, the yield of this reaction is not very good.

Low molecular weight linear polyorganosiloxanes having terminal silanol groups may be industrially manufactured by the hydrolysis of linear organochlorosiloxanes or chlorosilanes having chlorine atoms at both molecular ends in a weakly alkaline aqueous solution in order to prevent them from forming cyclic compounds. However, in this method, HCl produced by the hydrolysis may precede the condensation reaction, since silanol groups are unstable against acids and alkalis. As a result, higher molecular weight organopolysiloxanes and cyclic polysiloxanes or silanes are also produced in addition to the intended organopolysiloxanes or silanes. Therefore, this synthesis method is not particularly useful unless there is a means to maintain the hydrolysis water strictly neutral, which is difficult.

Another method known is the acetoxylation of the organochloropolysiloxanes with acetic acid, followed by hydrolysis. However, this method does not complete the hydrolysis fully and the residual acetoxyl groups remain in the product. Therefore, the product is not desirable as a dispersing agent for silicone rubber.

On the other hand, U.S. Pat. No. 3,925,285 discloses a synthetic method for low molecular weight linear polyorganosiloxanes having silanol terminal groups along with a small amount of residual methoxyl groups through the reaction of hexamethyl cyclotrisiloxane, methanol, formic acid, and water. This method is rather costly due to the employment of the relatively expensive hexamethyl cyclotrisiloxane. In addition, it will not form low molecular weight linear polyorganosiloxanes having silanol terminal groups with less than three D units [$(CH_3)_2SiO$]. Further, compounds shorter than 1,5-dihydroxy trisiloxane cannot be formed from this reaction. Thus, the content of hydroxyl groups is limited.

Further, U.S. Pat. No. 5,057,620 discloses a method wherein the corresponding chlorosiloxanes are added drop by drop to the epoxy type solvents containing water, such as propylene oxide and butylene oxide. Again in this method, the relatively expensive hexamethyl cyclotrisiloxane is utilized. In addition, there is a safety problem of electrostatic ignition when using a low boiling point solvent.

Further, Japanese Patent Application, Kokoku (examined) 64-5604 describes a synthesis method for short-chained silanols wherein alkoxy silanes are hydrolyzed by solid acid catalysts such as activated clay. In this method, it is necessary to neutralize the solid acid catalysts, which makes the process complicated. In addition, this method results in a mixture of various kinds of short-chained silanols and the yield for the dimer diol is about 50%. The yield of the monomer diol is at most 10% with 84% purity, as seen in Comparison Example 3 below.

U.S. Pat. No. 3,304,318 shows a method of manufacturing resins with a high degree of polymerization through the hydrolysis of alkoxy silanes by utilizing cation-exchange resins. However, this patent does not mention any application to the synthesis of short-chained silanols, particularly the synthesis of dimer diols or their yields.

The present invention was made, with a view to these deficiencies of the prior art, with the object of providing manufacturing methods for organosilanes having silanol groups, particularly diorganodihydroxy silanes, at a high yield, with a simple process, and at a low cost.

SUMMARY OF THE INVENTION

The present inventors, after extensive investigation to achieve the above-stated goal, have discovered that organosilanes having silanol groups which are useful as a dispersing agent for silicone rubber can be obtained from organoalkoxy silanes, such as relatively inexpensive dimethoxy dimethyl silane, by a simple process wherein organoalkoxy silanes, having at most 20 ppm content of chlorine, expressed by the general chemical formula (1) below:

$$Si(R^1)_m(R^2)_n(OR^3)_k \qquad (1)$$

wherein each of $R^1$ and $R^2$ are independently either a substituted or unsubstituted monovalent hydrocarbon group; $R^3$ is an alkyl group of 1 to 4 carbon atoms; subscripts m and n are 0, 1, 2, or 3; k is either 1 or 2; and the sum of subscripts m+n+k=4, are mixed with ion-exchanged water having an electroconductivity of at least $10^{10} M\Omega$, then a macro-porous cation-exchange resin with a pore volume measured by the mercury injection method of at least 0.1 ml/g is added, the mixture is stirred and the ion-exchange resin is removed.

The organosilanes having silanol groups which are prepared are preferably diol monomers of the formula (2):

$$Si(R^1)_m(R^2)_n(OH)_k \qquad (2)$$

wherein $R^1$, $R^2$, m, n and k are as defined above. Preferred monomers are of the formula HO—$SiR^1R^2$—OH, particularly HO—$SiMe_2$—OH, where Me is methyl.

Upon further study of the specification and appended claims, further objects and advantages of this invention will become apparent to those skilled in the art.

Below the present invention is explained in further detail. The manufacturing method of organosilanes having silanols at the molecular ends of the present invention includes mixing organoalkoxy silanes, having at most a 20 ppm content of chlorine, expressed by the general chemical formula (1) below:

$$Si(R^1)_m(R^2)_n(OR^3)_k \qquad (1)$$

wherein each of $R^1$ and $R^2$ is independently either a substituted or unsubstituted monovalent hydrocarbon group; $R^3$ is an alkyl group of 1 to 4 carbon atoms; subscripts m and n are 0, 1, 2, or 3; k is either 1 or 2; and the sum of subscripts m+n+k=4, with ion-exchanged water whose electroconductivity is at least $10^{10}M\Omega$, then adding a macro-porous cation exchange resin, followed by stirring the mixture and then removing the ion-exchange resin.

In the formula (1), each of $R^1$ and $R^2$ are independently either a substituted or unsubstituted monovalent hydrocarbon group, which is preferably of 1 to 10 carbon atoms, more preferably 1 to 6 carbon atoms. Examples thereof are: alkyl groups such as a methyl group, a propyl group, a butyl group, a pentyl group, a hexyl group, an octyl group, a decyl group and a dodecyl group; alkenyl groups such as a vinyl group; aryl groups such as a phenyl group and a tolyl group; aralkyl groups such as a β-phenyl ethyl group; and said hydrocarbon groups in which a part, or all, of the hydrogen atoms bound to carbon atoms are substituted by halogen atoms such as fluorine atoms or cyano groups (for example, a 3,3,3-trifluoropropyl group and a cyanoethyl group). Among the groups for $R^1$ and $R^2$, a methyl group, a vinyl group, and a phenyl group are particularly desirable.

Each $R^3$ is independently selected from alkyl groups of 1 to 4 carbon atoms and preferably a methyl group or an ethyl group, both of which may exist within the molecule at the same time.

Examples of the organoalkoxy silanes of formula (1) are: dialkoxy silanes such as dimethyl dimethoxy silane, phenyl methyl dimethoxy silane, methyl vinyl dimethoxy silane, dimethyl diethoxy silane, and phenyl methyl methoxy ethoxy silane; and monoalkoxy silanes such as dimethyl vinyl methoxy silane, trimethyl methoxy silane, and dimethyl phenyl methoxy silane. Trialkoxy silanes and tetraalkoxy silanes are not desirable since they undergo a condensation reaction. When utilized in the process for preparing a dispersing agent for silicone rubber compounds, dialkoxy silanes are desirable and dimethyl dimethoxy silane is particularly preferable. These organoalkoxy silanes may be employed in the process singly or in a combination of two or more such organoalkoxy silanes. When a combination of alkoxy silanes are used, their hydrolysis rates may differ, leading to the possibility of a non-uniform reaction; therefore, caution is needed for such use.

Further, it is recommended to employ organoalkoxy silanes with low chlorine content. The short-chained silanols, which are the intended product of the present invention, are unstable under both acidic and alkaline conditions. Therefore, the system must be maintained neutral during the reaction and distillation conducted under reduced pressure in order to obtain the short-chained silanols. In general, alkoxy silanes are synthesized from the corresponding chlorosilanes, thus, unreacted chlorosilanes remain in the alkoxy silanes. These chlorosilanes swiftly react with water and form hydrochloric acid. Therefore, the existence of chlorosilanes makes the reaction system acidic, which leads to the undesirable silanol condensation. As a result, organoalkoxy silanes with low chlorosilane content must be used in order to obtain the short-chained silanols. Accordingly, the chlorine content should be at most 20 ppm, more preferably at most 10 ppm, in the organoalkoxy silanes.

Ion-exchanged water is an essential reagent in the present invention for performing the hydrolysis of the organoalkoxy silanes. Ions such as Na, Ca, and Mg are eliminated by ion-exchange resins from the water so that the electroconductivity of the resultant ion-exchanged water is at least $10^{10}M\Omega$. It is particularly preferred that the hydrolysis is performed at relatively low temperature and at the condition with many silanol groups. When the conductivity is less than this level, ions contained in the ion-exchange resin and hydrolysis water start to ion-exchange, making the hydrolysis water acidic. As a result, the intended product short-chained silanols cannot exist stably. The electroconductivity of ion exchanged water is preferably at least $10^{12}M\Omega$, more preferably at least $10^{15}M\Omega$.

A shortage in the amount of water employed for the hydrolysis results in problems such as incomplete hydrolysis of the alkoxyl groups, which results in the formation of less hydroxyl groups. Therefore, the molar amount of water is preferably from 0.5 to 10 moles per alkoxyl group in the organoalkoxy silane, more desirably from 1 to 5 moles.

In the present invention, a macro-porous cation-exchange resin is added to the mixture of the organoalkoxy silanes and the ion-exchanged water. This macro-porous cation-exchange resin is an essential component for providing a mild hydrolysis while maintaining a pH value of the hydrolysis water around neutral. The preferred amount of its addition is from 0.00001 to 30 weight % based on the total weight of the organoalkoxy silanes and the ion-exchanged water, more desirably from 0.001 to 1 weight %. More than this amount of the ion-exchange resin will predominantly result in condensation of the formed silanol groups, which hinders formation of the short-chained silanol products. On the other hand, a lesser amount will not provide enough activity necessary for hydrolysis, leading to residual alkoxyl groups, and an insufficient silanol content in the product.

As the cation-exchange resin, suspension-polymerized polymers with polystyrene or divinyl benzene skeletons are desirable. Types of cation-exchange resins are divided, for example, into a gel type and a macro-porous type. The gel type resin does not possess pores; therefore, the substances being exchanged hardly enter the inside of the resin, which makes it difficult to effectively utilize the activity points. On the other hand, the macro-porous type resin possesses large pores; therefore, the substances being exchanged easily reach the activity points and utilize them more effectively. Therefore, the cation exchange resins utilized in the present invention are necessarily macro-porous. The pore volume of such resins, measured by the mercury injection method, is preferably at least 0.1 ml/g. Further, acidic groups attached to the resin may be a sulfonic group, an acrylic group and so on. The H+ type resin is preferred and the sulfonic group resin is particularly preferred. Example of the cation exchange resins which satisfy the criteria are: Amberlyst 15 (manufactured by Rohm & Haas); Dia-ion PK-208H, PK-216H, and PK-228H (all manufactured by Mitsubishi Kasei); and Purolyte CT-175, CT-171, and CT-169 (all manufactured by Purolyte). Among them, Purolyte CT-175 (manufactured by Purolyte) is particularly desirable.

In the present invention, the mixture is stirred after the addition of the cation-exchange resin for the hydrolysis of the organoalkoxy silanes in order to obtain the short-chained silanols. In this case, the preferred stirring time (reaction time) is at least 3 minutes, more preferably at least 5 minutes. Further, the reaction temperature is preferably at least 0° C. However, there is a possibility for the silanols produced by the hydrolysis to condense when the reaction time is too long; therefore, less than 3 hours of reaction time is preferred to produce the short-chained silanols. In addition, the condensation of silanols may occur at high reaction temperature; therefore, the reaction temperature is preferably from 0° to 50° C.

In one embodiment, the hydrolysis process may be conducted in a continuous manner, controlled to provide the designed residence time.

According to the method of the present invention, the hydrolysis is performed by the cation-exchange resin with the organoalkoxy silanes and water. Therefore, at the beginning of the hydrolysis, the organoalkoxy silane phase and the water phase are separated. As the hydrolysis proceeds, water is consumed, and alcohol is produced, which makes the system not homogeneous. Therefore, the reaction is preferably carried out with sufficient stirring and mixing, for example, to keep the silane and water phases in intimate contact, and in contact with the cation-exchange resin surfaces. The cation-exchange resin is solid, and does not dissolve into the solution. Thus, the reaction takes place on the solid surface of the resin. As a result, insufficient stirring and mixing may result in a non-uniform reaction.

After the reaction, the cation-exchange resin is removed. The cation-exchange resin, which is a hydrolysis catalyst, may be easily removed from the reaction mixture by methods such as filtration. After such filtration, the hydrolysis and silanol condensation reaction will stop, without the need to add neutralizing agents such as alkalis. The cation-exchange resins separated from the reaction mixtures may be re-utilized as the hydrolysis catalyst for the process without any special treatments.

After the removal of the cation-exchange resins, the reaction mixture may be stripped to remove the volatile components such as alcohols and trace amounts of residual water. The stripping conditions are preferably selected to avoid stripping of the intended silanols. The pressure for the stripping is not critical; however, the preferred temperature is at most 80° C. considering the stability of silanols.

Organosilanes having silanol groups obtained by the present invention are manufactured at high yield, by an uncomplicated process, and at low cost. In addition, the obtained organosilanes are solid at room temperature; therefore, they may be easily separated from the trimer or larger organosiloxanes which are liquid, for example, by the methods of filtration, or by phase separation with toluene or hexane.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding Japanese Patent Publication No. 6-049820, filed Feb. 23, 1994, are hereby incorporated by reference.

EXAMPLES

Below, the invention is demonstrated by using Examples and Comparison Examples. However, the invention is not limited to these Examples.

Example 1

Hydrolysis of dimethyl dimethoxy silane

In a 200 ml capacity flask equipped with a thermometer and a stirrer, with its atmosphere replaced by $N_2$, 40.0 g (2.23 mol) of ion-exchanged water having electroconductivity of $10^{15} M\Omega$ was added to 85.5 g (0.711 mol) of dimethyl dimethoxy silane (with 5 ppm of chlorine content) to form a binary phase system. Further, 0.093 g (0.0805 weight %) of a cation-exchange resin (CT-175, pore volume size measured by mercury injection method of 0.49 ml/g, manufactured by Purolyte) was added to the mixture and stirred for 15 minutes at 20° C. to make the solution phase uniform. The mixture was stirred another 15 minutes; then the solid ion-exchange resin was removed by filtration. After removal of water and the by-product, methanol, under the condition of 20° C. at 5 mmHg, 60.8 g of a white plate-like crystal was obtained. This white crystal was dissolved into THF and analyzed by gas chromatography. The result showed that the crystal contained 76.1 mol % of dimethyl dihydroxy silane and 17.0 mol % of tetramethyl disiloxane diol (the yield for dimethyl dihydroxy silane was 70.4 %).

Example 2

The hydrolysis was performed by the same method as described in Example 1 above, except the cation-exchange resin separated by filtration in Example 1 was utilized again without any special treatments as a hydrolysis catalyst.

After repeating this process 10 times, the obtained white crystal was dissolved into THF and analyzed by gas chromatography. The result showed that the crystal contained 72.7 mol % of dimethyl dihydroxy silane and 15.1 mol % of tetramethyl disiloxane diol (the yield for dimethyl dihydroxy silane was 67.3 %).

The above results confirmed that the ion-exchange resin can be recoverable and reusable without any special treatment.

Comparison Example 1

In a 50 ml capacity flask equipped with a thermometer and a stirrer, with its atmosphere replaced by $N_2$, 6.58 g (0.366 mol) of hydrochloric acid solution with pH 4.2 was added to 20.0 g (0.166 mol) of dimethyl dimethoxy silane. The maximum temperature of the mixture reached to 40° C. and it formed a uniform solution. After stirring 5 minutes, 0.2 g of magnesium oxide ($4.96 \times 10^{-3}$ mol) and 15 g of magnesium sulfate (0.125 mol) were added and further stirred for 3 hours. The oily mixture was stripped at 20° C., under the pressure of 5 mmHg, after filtration. Analysis of the oily product by gas chromatography showed that the product contained 15.7 mol % of tetramethyl disiloxane diol, 24.4 mol % of hexamethyl trisiloxane diol, and 9.3 mol % of decamethyl pentasiloxane diol.

By this method, condensation of silanol groups occurred and only the condensed products, but not dimethyl dihydroxy silane, were obtained.

Comparison Example 2

The Comparison Example 2 followed the method described in Example 1, except that a gel type cation exchange resin (CT-100S, manufactured by Purolyte, pore volume of less than 0.1 which was measured by the mercury injection method) was employed as a hydrolysis catalyst.

In a 200 ml capacity flask equipped with a thermometer and a stirrer, with its atmosphere replaced by $N_2$, 6.58 g (0.557 mol) of the cation-exchanged water having electroconductivity of $10^{10} M\Omega$ was added to 28.5 g (0.237 mol) of dimethyl dimethoxy silane to form a binary phase system. Further, 0.030 g (0.0809 weight %) of a cation-exchange resin (CT-100S, manufactured by Purolyte) was added to the mixture and stirred for 2 minutes at 20° C. The reaction solution remained as two separate phases and was not homogeneous, and the raw material, dimethyl dimethoxy silane was recovered.

This result indicates that the cation-exchange resin with a small pore volume offers only a low catalytic activity in hydrolysis, which is not adequate.

Comparison Example 3

In a 50 mol capacity flask equipped with a thermometer and a stirrer, with its atmosphere replaced by $N_2$, 10.0 g (0.556 mol) of the ion-exchanged water was added to 20.0 g (0.166 mol) of dimethyl dimethoxy silane (with 200 ppm of chlorine content). Further, 0.093 g of a cation-exchange resin (CT-175, pore volume size measured by mercury injection method of 0.49 ml/g, manufactured by Purolyte) was added to the mixture and stirred vigorously. After 10 minutes of stirring, the solution became uniform. After stirring another 15 minutes, the mixture was filtered to remove the ion-exchanger resin. The water and the by-product, methanol, were stripped under the condition of 20° C. at 5 mmHg, and 13.5 g of colorless, transparent oily product was obtained. This oily product was analyzed by gas chromatography. The result showed that the oily product contained 3.7 mol % of dimethyl dihydroxy silane, 29.1 mol % of tetramethyl disiloxane diol, 24.4 mol % of hexamethyl trisiloxane diol, 15.0 mol % of octamethyl tetrasiloxane diol, and 2.8 mol % of decamethyl pentasiloxane diol (the yield for dimethyl dihydroxy silane was 3.4 %).

The content of dimethyl dihydroxy silane is less than that obtained in Example 1 and the products with two or more siloxane units have increased, which suggests that the condensation was in progress.

Example 3

In a 50 ml capacity flask equipped with a thermometer and a stirrer, with its atmosphere replaced by $N_2$, 7.30 g (0.406 mol) of the ion-exchanged water was added to 20.0 g (0.135 mol) of diethyl dimethoxy silane (with a chlorine content of at most 1 ppm). Further, 0.085 g (0.311 weight %) of a cation-exchange resin (CT-175, pore size measured by mercury injection method of 0.49 ml/g, manufactured by Purolyte) was added to the mixture and stirred for about 13 minutes to make the solution phase uniform. The mixture was stirred another 15 minutes, then the ion-exchange resin was removed by filtration. After removal of the volatile by-product, methanol, under the condition of 20° C. at 5 mmHg, 12.4 g of a white crystal was obtained. This white crystal was dissolved into THF and analyzed by gas chromatography. The result showed that the crystal contains 71 mol % of diethyl dihydroxy silane (the yield for diethyl dihydroxy silane was 52.8%).

Example 4

In a 50 ml capacity flask equipped with a thermometer and a stirrer, with its atmosphere replaced by $N_2$, 6.74 g (0.374 mol) of the ion-exchanged water was added to 20.0 g (0.125 mol) of methyl vinyl diethoxy silane (with a chlorine content of at most 1 ppm). Further, 0.021 g (0.0785 weight %) of a cation-exchange resin (CT-175, pore size measured by mercury injection method of 0.49 ml/g, manufactured by Purolyte) was added to the mixture and stirred at room temperature for about 70 minutes to make the solution phase uniform, and the mixture was stirred another 80 minutes. After the cation-exchange resin was removed by filtration, stripping was performed under the condition of 20° C. at 5 mmHg, which resulted in 11.9 g of a white plate-like solid. This white solid was dissolved into THF and analyzed by gas chromatography. The result showed that the solid contained 75.1 mol % of methyl vinyl dihydroxy silane and 15.3 mol % of 1,3-dimethyl-1-,3-divinyl-1,3-dihydroxy siloxane (the yield for dimethyl vinyl dihydroxy silane was 68.7%).

Example 5

Hydrolysis of methoxy trimethyl silane

In a 50 ml capacity flask equipped with a thermometer and a stirrer, with its atmosphere replaced by $N_2$, 20.0g(0.192 mol) of methoxy trimethyl silane (with a chlorine content of 20 ppm) and 4.1g (0.228 mol) of ion-exchanged water having electroconductivity of $10^{15}$MΩ were added. Further, 0.090g (0.37 weight %) of a cation-exchange resin (CT-175, manufactured by Purolyte, pore volume size measured by the mercury injection method of 0.49 ml/g.) was added to the mixture and stirred for 60 minutes at 20° C.

After the solid ion-exchange resin was removed by filtration and methanol, as a by-product, was removed under the conditions of 20° C. at 5 mmHg, 15. 1 g of clear and transparent liquid was obtained.

Analyzed by gas chromatography, the liquid contained 91.5 mol % of trimethyl silanol and the yield was 80.0%.

According to the present invention, organosilanes having silanol groups which are useful as a dispersing agent in silicone rubbers may be obtained by a simple process from organoalkoxy silanes such as relatively inexpensive dimethoxy dimethyl silane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for manufacturing organosilanes having silanol groups comprising: mixing an organoalkoxy silane, having at most a 20 ppm content of chlorine, expressed by the chemical formula (1) below:

$$Si(R^1)_m(R^2)_n(OR^3)_k \qquad (1)$$

wherein each of $R^1$ and $R^2$ is independently either a substituted or unsubstituted monovalent hydrocarbon group; $R^3$ is an alkyl group of 1 to 4 carbon atoms; subscripts m and n are 0, 1, 2, or 3; k is either 1 or 2; and the sum of subscripts m+n+k=4, with ion-exchanged water having an electroconductivity of at least $10^{10}$MΩ, then further adding a macro-porous cation-exchange resin, with a pore volume measured by the mercury injection method of at least 0.1 ml/g, to the mixture, stirring the mixture, removing the cation-exchange resin from the mixture and recovering an organosilane with at least one terminal silanol group.

2. The method of claim 1, wherein the molar amount of the ion-exchanged water used is from 0.5 to 10 moles per alkoxyl groups in the organoalkoxy silane and the amount of the macro-porous cation-exchange resin used is 0.00001 to 30 weight % based on the total weight of the organoalkoxy silanes and ion-exchanged water.

3. The method of claim 2, wherein the molar amount of the ion-exchanged water used is from 1 to 5 moles per alkoxyl groups in the organoalkoxy silane, and the amount of the macro-porous cation-exchange resin used is from 0.001 to 1 weight % based on the total weight of the organoalkoxy silanes and ion-exchanged water.

4. The method of claim 1, wherein the organoalkoxy silane is a dialkoxy silane.

5. The method of claim 4, wherein the dialkoxy silane is dimethyl dimethoxy silane.

6. The method of claim 1, wherein, in formula (1), $R^1$ and $R^2$ are each independently a monovalent hydrocarbon group of 1 to 10 carbon atoms, optionally substituted by halogen or cyano groups.

7. The method of claim 1, wherein the electroconductivity of the ion-exchanged water is at least $10^{12} M\Omega$.

8. The method of claim 1, wherein the mixture is stirred for 3 minutes to 3 hours at a temperature of 0° to 50° C.

9. The method of claim 1 conducted as a continuous method.

10. The method of claim 1, further comprising re-using the removed cation-exchange resin for a subsequent method according to claim 1.

11. The method of claim 1, wherein the product organosilanes containing silanol groups comprises at least one monomer compound of the formula (2):

$$Si(R^1)_m(R^2)_n(OH)_k \qquad (2)$$

wherein $R^1$, $R^2$, m, n and k are as defined in claim 1.

12. The method of claim 11, wherein the product comprises at least one monomer compound of the formula HO—SiR$^1$R$^2$—OH.

13. The method of claim 11, wherein the product comprises at least one monomer compound of the formula HO—SiMe$_2$—OH, where Me is methyl.

14. The method of claim 6, wherein $R^1$ and $R^2$ are each independently an alkyl, alkenyl or aralkyl group of 1 to 10 carbon atoms, optionally substituted by halogen or cyano groups.

15. The method of claim 1, wherein each $R^3$ group is independently a methyl or ethyl group.

16. The method of claim 1, wherein the organoalkoxy silane has a chlorine content of at most 10 ppm.

17. The method of claim 1, wherein the electroconductivity of the ion-exchanged water is at least $10^{15} \Omega$.

* * * * *